United States Patent
Mehta et al.

(10) Patent No.: US 12,171,506 B2
(45) Date of Patent: Dec. 24, 2024

(54) TOUCHLESS CONTROL OF SURGICAL DEVICES

(71) Applicants: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

(72) Inventors: Dhairya Mehta, Medford, MA (US); Brian William Quist, Salem, MA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 0 days.

(21) Appl. No.: 18/003,266

(22) PCT Filed: Jul. 15, 2021

(86) PCT No.: PCT/US2021/041738
§ 371 (c)(1),
(2) Date: Dec. 23, 2022

(87) PCT Pub. No.: WO2022/015923
PCT Pub. Date: Jan. 20, 2022

(65) Prior Publication Data
US 2023/0248449 A1 Aug. 10, 2023

Related U.S. Application Data

(60) Provisional application No. 63/053,347, filed on Jul. 17, 2020.

(51) Int. Cl.
*A61B 34/00* (2016.01)
*G06F 3/01* (2006.01)
*G06F 3/16* (2006.01)

(52) U.S. Cl.
CPC .............. *A61B 34/25* (2016.02); *G06F 3/017* (2013.01); *G06F 3/167* (2013.01)

(58) Field of Classification Search
CPC .......... A61B 34/25; G06F 3/017; G06F 3/167
See application file for complete search history.

(56) References Cited

U.S. PATENT DOCUMENTS

| 6,591,239 B1 | 7/2003 | Mccall et al. |
| 7,286,992 B2 | 10/2007 | Sander et al. |

(Continued)

FOREIGN PATENT DOCUMENTS

| WO | 20100045313 A1 | 4/2010 |
| WO | 20170175232 A1 | 10/2017 |

OTHER PUBLICATIONS

International Searching Authority, International Application No. PCT/US2021/041738, International Filing Date: Jul. 15, 2021, International Search Report and Written Opinion dated Nov. 17, 2021.

*Primary Examiner* — Gene W Lee
(74) *Attorney, Agent, or Firm* — Dickinson Wright PLLC; Mark E. Scott

(57) ABSTRACT

Touchless control of surgical devices. One example is a method of performing a surgical procedure, the method comprising: receiving, by a touchless-interface controller, a touchless command directly identifying an operational parameter of a target surgical controller of a plurality of surgical controllers used for performing the surgical procedure; generating, by the touchless-interface controller, a command value from the touchless command; and communicating, by the touchless-interface controller, a control command to the target surgical controller of the plurality of surgical controllers based on the command value.

22 Claims, 6 Drawing Sheets

(56) References Cited

U.S. PATENT DOCUMENTS

| | | | |
|---|---|---|---|
| 9,390,726 B1* | 7/2016 | Smus | G06F 3/017 |
| 2001/0034530 A1* | 10/2001 | Malackowski | A61B 34/20 |
| | | | 606/130 |
| 2002/0095294 A1* | 7/2002 | Korfin | G06F 3/167 |
| | | | 704/E15.04 |
| 2006/0052661 A1* | 3/2006 | Gannot | A61B 1/042 |
| | | | 606/11 |
| 2006/0142740 A1 | 6/2006 | Sherman et al. | |
| 2009/0163898 A1* | 6/2009 | Gertner | A61B 3/113 |
| | | | 606/4 |
| 2011/0201886 A1* | 8/2011 | Gumbs | A61B 1/00066 |
| | | | 600/118 |
| 2011/0302538 A1* | 12/2011 | Vennelakanti | G06F 1/3228 |
| | | | 713/323 |
| 2014/0247208 A1* | 9/2014 | Henderek | G06F 3/017 |
| | | | 345/156 |
| 2015/0290031 A1* | 10/2015 | Wellhoefer | G06F 3/03 |
| | | | 345/156 |
| 2016/0106582 A1* | 4/2016 | Campos | A61F 9/009 |
| | | | 606/4 |
| 2016/0113760 A1* | 4/2016 | Conrad | A61F 2/1648 |
| | | | 623/6.22 |
| 2018/0140348 A1* | 5/2018 | Merschon | A61B 18/1206 |
| 2018/0168755 A1 | 6/2018 | Cagle et al. | |
| 2019/0029769 A1 | 1/2019 | Martin | |
| 2019/0201104 A1* | 7/2019 | Shelton, IV | G16H 30/40 |
| 2019/0201140 A1* | 7/2019 | Yates | A61B 34/25 |
| 2019/0314005 A1* | 10/2019 | Ishihara | A61B 34/74 |
| 2020/0142505 A1* | 5/2020 | Choi | G08C 21/00 |
| 2021/0145642 A1* | 5/2021 | Berlin | A61M 27/002 |

* cited by examiner

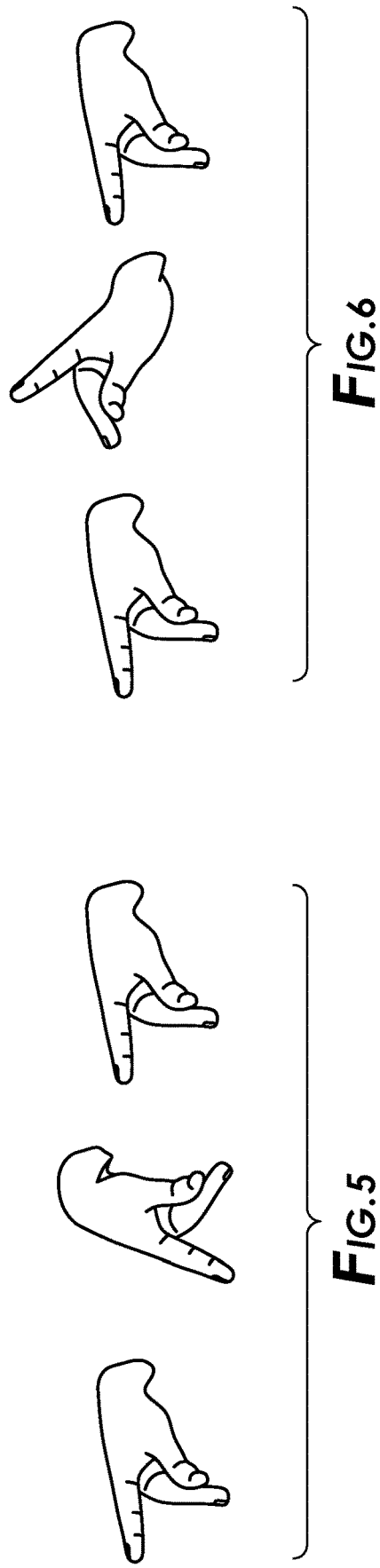
FIG. 5
FIG. 6
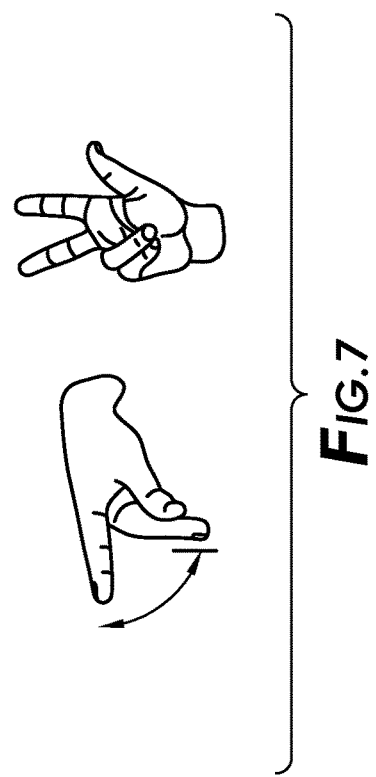
FIG. 7

TOUCHLESS CONTROL OF SURGICAL DEVICES

CROSS-REFERENCE TO RELATED APPLICATIONS

This application is a U.S. National Phase Entry of PCT application number PCT/US2021/041738 filed Jul. 15, 2021 titled "Methods and Systems of Touchless Control of Surgical Devices." The PCT application claims the benefit of U.S. Provisional Application Ser. No. 63/053,347 filed Jul. 17, 2020 and titled "AI-Enabled Control of the Arthroscopic Technology Tower." Both the PCT application and the provisional application are incorporated by reference herein as if reproduced in full below.

BACKGROUND

Endoscopic and arthroscopic surgical procedures may utilize a device stack or tower upon and within which multiple devices are placed that enable the surgical procedure. For example, a tower may include a visualization system for interfacing with an endoscopic or arthroscopic device and displaying images on a display device, a controller for mechanical resection instrument, a controller for a plasma-based ablation or COBLATION® brand system, and a fluid-management controller for control of inflow and outflow from the surgical site. Each device may implement multiple settings that are often changed or updated throughout the course of the surgical procedure. For example, a surgeon may change the speed of the mechanical resection instrument, change a power setting used by the plasma-based ablation system, or change the pressure or flow setting used by the fluid-management controller.

As the surgeon is within the sterile field of the surgical procedure, and the controllers for the various devices are outside the sterile field, in the related art a circulating nurse outside of the sterile field manually interfaces with the devices based on instructions of the surgeon. Sometimes the manual interface may be as simple as a single button press. In other situations, the manual interface requires accessing and navigating through a menu structure to find the parameter to be changed. As a last resort, the surgeon may also "scrub-out", manually change the parameter, and then scrub back into the surgery.

SUMMARY

One example is a method of performing a surgical procedure, the method comprising: receiving, by a touchless-interface controller, a touchless command directly identifying an operational parameter of a target surgical controller of a plurality of surgical controllers used for performing the surgical procedure; generating, by the touchless-interface controller, a command value from the touchless command; and communicating, by the touchless-interface controller, a control command to the target surgical controller of the plurality of surgical controllers based on the command value.

In the example method, receiving the touchless command may further comprise receiving a natural-language command by way of a microphone communicatively coupled to the touchless-interface controller; and generating the command value may further comprise generating the command value from a predefined list of command values using the natural-language command. Generating the command value using the natural-language command may further comprises generating the command value by the touchless-interface controller without the touchless-interface controller communicating the natural-language command to a remote computer system. In some examples the natural-language command does not contain reference to movement between levels of a menu structure. In the example method, receiving the touchless command may further comprise receiving a gesture (e.g., a hand gesture) by way of a camera communicatively coupled to the touchless-interface controller; and generating the command value may further comprise generating the command value based on matching the gesture to a predefined list of gestures. Receiving the gesture may further comprise receiving a hand gesture that identifies both the target surgical controller and direction of change of a parameter associated with the target surgical controller.

Prior to receiving the touchless command, the example method may further comprise receiving a wake command by the touchless-interface controller. Receiving the wake command may further comprise receiving a verbal command by way of a microphone communicatively coupled to the touchless-interface controller. In the example method, receiving the touchless command may further comprises receiving a natural-language command by way of a microphone communicatively coupled to the touchless-interface controller; and generating the command value may further comprise generating the command value from a predefined list of command values using the natural-language command. In other cases, receiving the touchless command may further comprise receiving a gesture by way of a camera communicatively coupled to the touchless-interface controller; and generating the command value may further comprise generating the command value based on matching the gesture to a predefined list of gestures. Receiving the wake command may further comprise detecting, by the touchless-interface controller, that a surgeon's gaze has dwelled on the target surgical controller or a depiction of the target surgical controller for a predetermined amount of time. Receiving the wake command may further comprise receiving a physical input being at least one selected from a group comprising: a foot switch; and camera head button press.

Other examples include a surgical system comprising: a first surgical controller communicatively coupled to a device-cart network; a second surgical controller communicatively coupled to the device-cart network; a touchless-input device; and a touchless-interface controller communicatively coupled to the device-cart network and the touchless-input device. The example touchless-interface controller may be configured to: receive a touchless command directly identifying an operational parameter of a target surgical controller of the first and second surgical controllers; generate a command value from the touchless command; and communicate, by way of the device-cart network, a control command to the target surgical controller by way of the device-cart network, the control command based on the command value.

In the example system, the touchless-input device may further comprise a microphone; and when the touchless-interface controller receives the touchless command, the touchless-interface controller may be further configured to receive a natural-language command by way of the microphone; and when the touchless-interface controller generates the command value, the touchless-interface controller may be further configured to generate the command value from a predefined list of command values using the natural-language command. When the touchless-interface controller generates the command value using the natural-language command, the touchless-interface controller may be further configured to generate the command value without the touchless-interface controller communicating the natural-language command to a remote computer system. In one example, the natural-language command does not contain reference to movement between levels of a menu structure.

In the example system, the touchless-input device may further comprises a camera; and when the touchless-interface controller receives the touchless command, the touchless-interface controller may be further configured to receive a gesture by way of the camera; and when the touchless-interface controller generates the command value, the touchless-interface controller may be further configured to generate the command value based on matching the gesture to a predefined list of gestures. When the touchless-interface controller receives the gesture, the touchless-interface controller may be further configured to receive a hand gesture that identifies both the target surgical controller and direction of change of a parameter associated with the target surgical controller.

In the example system, the touchless-interface controller may be is further configured to receive a wake command. When the touchless-interface controller receives the wake command, the touchless-interface controller may be further configured to receive a verbal command by way of a microphone. When the touchless-interface controller receives the wake command, the touchless-interface controller may be further configured to detect that a surgeon's gaze has dwelled on the target surgical controller or a depiction of the target surgical controller for a predetermined amount of time.

In the example system, the first and second surgical controllers may be each at least one selected from a group comprising: an arthroscopic video controller; and endoscopic video controller; a resection controller; an ablation controller; a Virtual Reality (VR) headset; an Augmented Reality (AR) headset; a Mixed Reality (MR) headset; a vacuum pump; a patient-positioning system; a robotic arm; an ultrasonic cutting device; an insufflator; a patient-positioning system; and a robotic surgical system.

BRIEF DESCRIPTION OF THE DRAWINGS

For a detailed description of example embodiments, reference will now be made to the accompanying drawings in which:

FIG. 5 shows an example hand gesture in accordance with at least some embodiments;

FIG. 6 shows an example hand gesture in accordance with at least some embodiments;

FIG. 7 shows a combination hand gesture in accordance with at least some embodiments.

DEFINITIONS

Figure 1:
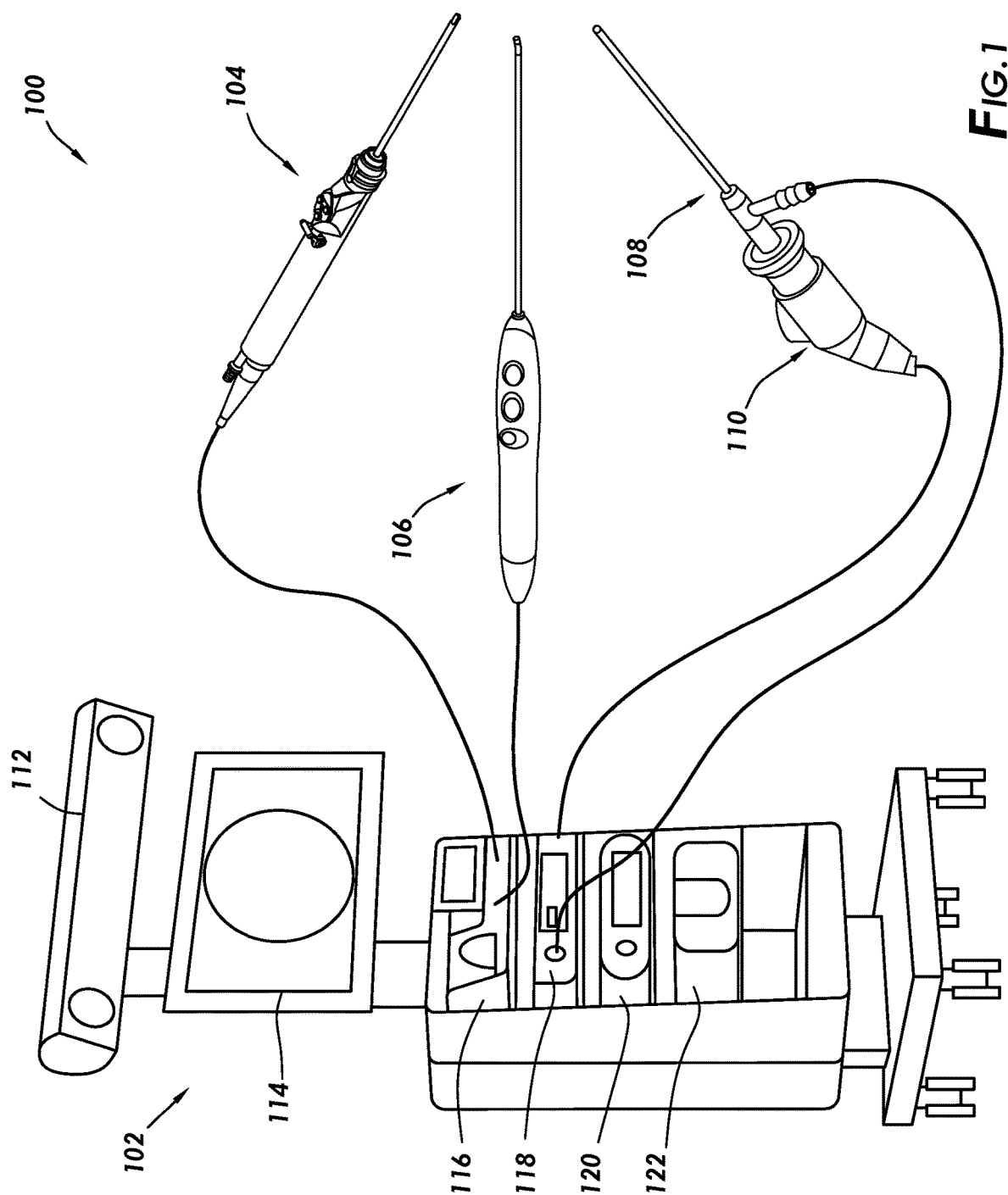
FIG. 1 shows a surgical system in accordance with at least some embodiments.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Natural-language command" shall mean a spoken full or partial sentence that instructs a change of an operational parameter. Natural-language command shall include sentences where the subject is of the "you-understood" form (e.g., "Turn up the joint pressure" is the "you-understood" form of "You turn up the joint pressure"). Natural-language command shall also include sentences where the verb is understood from the context (e.g., "video on" is both the "verb-understood" and the "you-understood" form of "You turn the video on").

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various examples are directed to touchless control of surgical devices. In particular, some examples are directed to touchless commands directed to a touchless-interface controller, where each touchless command directly identifies an operational parameter of a target surgical controller. For example, a touchless command may directly identify an operational parameter of a controller for a mechanical resection device, or an operation parameter of a controller for a plasma-based ablation device. More particular still, some examples are directed to the touchless-interface controller receiving a natural-language command by way of a microphone coupled to the touchless-interface controller. In example cases the natural-language command identifies the operational parameter and a magnitude and/or direction of change without the surgeon needing to navigate a menu structure. Other examples are directed to the touchless-interface controller receiving a hand gesture by way of a camera coupled to the touchless-interface controller. In example cases the hand gesture identifies the operational parameter and a magnitude and/or direction of change without the surgeon needing to navigate a menu structure. The specification first turns to an example system to orient the reader.

FIG. 1 shows a surgical system (not to scale) in accordance with at least some embodiments. In particular, the example surgical system 100 comprises a tower or device cart 102, an example mechanical resection instrument 104, an example plasma-based ablation instrument 106 (hereafter just ablation instrument 106), and an example arthroscope 108 and attached camera head 110. The device cart 102 may comprise a camera 112 (illustratively shown as a stereoscopic camera), a display device 114, a resection controller 116, a camera control unit (CCU) or endoscopic light source and video controller 118 (hereafter just video controller 118), a touchless-interface controller 120, and a pump controller 122 (e.g., single or dual peristaltic pumps). Fluidic connections of the mechanical resection instrument 104 and ablation instrument 106 are not shown so as not to unduly complicate the figure. Similarly, fluid connections between pump controller 122 and the patient are not shown so as not to unduly complicate the figure. In the example system, both the mechanical resection instrument 104 and the ablation instrument 106 are coupled to the resection controller 116 being a dual-function controller. In other cases, however, there may be a mechanical resection controller separate and distinct from an ablation controller. The example devices and controllers associated with the device cart 102 are merely examples, and other examples include Virtual Reality (VR) headset and related controllers, Augmented Reality (AR) headsets and related controllers, Mixed Reality (MR) systems and related controllers, vacuum pumps, patient-positioning systems, robotic arms holding various instruments, ultrasonic cutting devices and related controllers, patient-positioning controllers, an insufflator, and robotic surgical systems.

Figure 2:
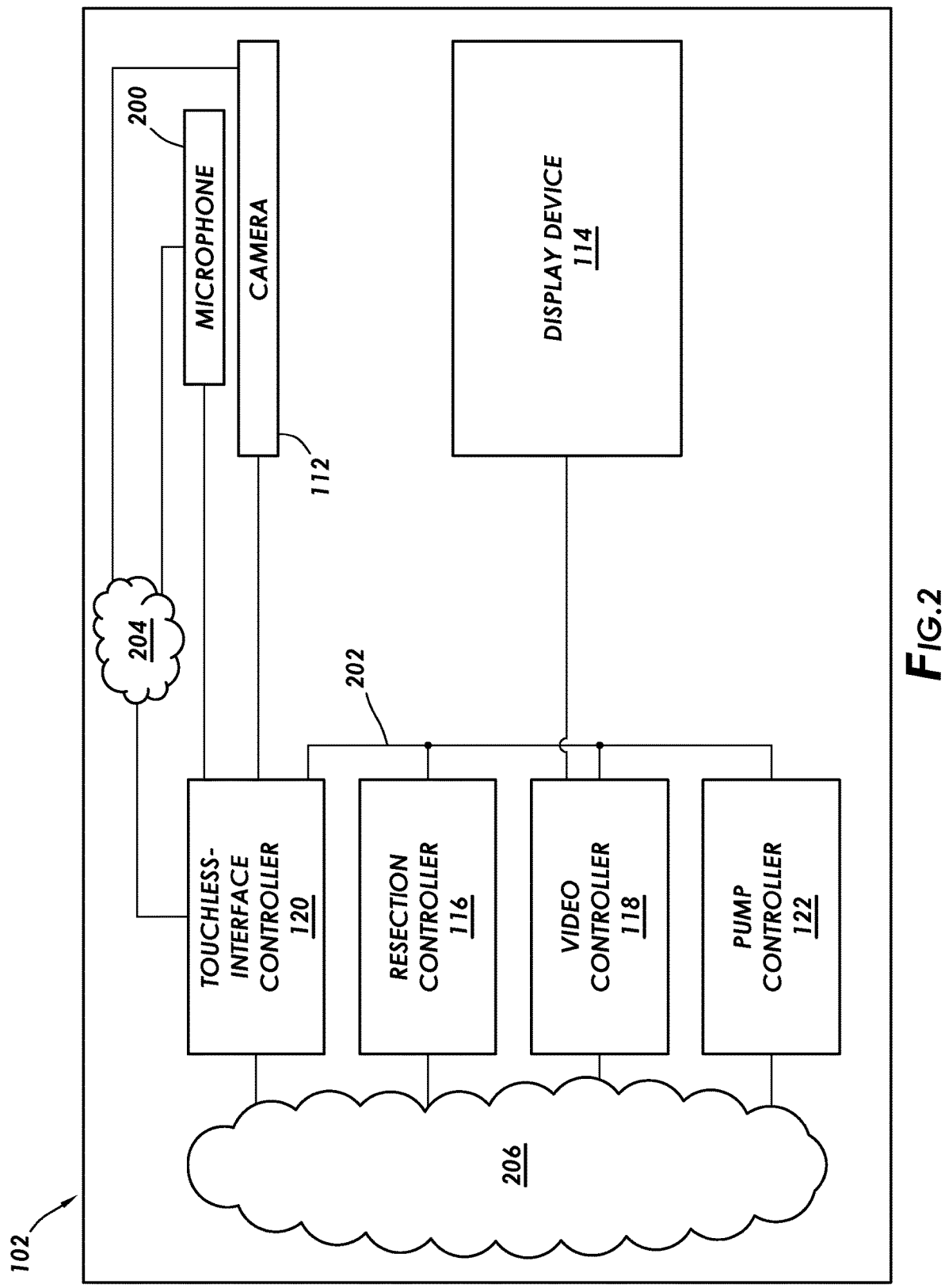
FIG. 2 shows a block diagram of the systems of the device cart in accordance with at least some embodiments.

FIG. 2 shows a block diagram of the example systems of the device cart 102. In particular, the example device cart 102 comprises the touchless-interface controller 120 operationally coupled to the camera 112. In some cases, the touchless-interface controller 120 may perform additional functions, such as tracking the location of objects within the surgical room (e.g., tracking location of fiducial arrays within the three-dimensional coordinate space of a stereoscopic camera), and thus the camera 112 may be a stereoscopic camera as shown in FIG. 1. In cases where location of objects within the 3D coordinate space of the camera system is not used, camera 112 may be a single-lens camera system suitable for receiving images and creating image signals of hand gestures and body-position gestures of the surgeon. In some cases, the camera 112 may be coupled to the touchless-interface controller 120 by way of a hardwired connection. In yet still other cases, the operational connection between the touchless-interface controller 120 and the camera 112 may take place wirelessly, as shown by wireless connection 204. The wireless connection 204 may take any suitable form, such as wireless network operated under any suitable network specification (e.g., Bluetooth, IEEE 802.11).

FIG. 2 also shows that in some embodiments the touchless-interface controller 120 may be operationally coupled to a microphone 200 to receive sounds and create signals based on voices within the surgical room. The example of FIG. 2 shows the microphone 200 being a member of the device cart 102 and coupled to the touchless-interface controller 120 by way of a hardwired connection. In other cases, the microphone 200 may be communicatively coupled to the touchless-interface controller 120 by way of a wireless connection, such as wireless connection 204. Further still, rather than being a member of the device cart 102, the microphone may be worn by the surgeon and communicatively coupled to the touchless-interface controller 120 by way of a wireless connection (e.g., Bluetooth, IEEE 802.11).

In the example system, the touchless-interface controller 120 is communicatively coupled to the resection controller 116, the video controller 118, the pump controller 122, and any other devices or controllers the surgeon chooses to have installed on the device cart 102. In some cases, the touchless-interface controller 120 is coupled the various other devices and controllers by hardwired connection, as shown by connection 202. Hardwired connection 202 may take any suitable form, such as local-area network (e.g., Ethernet) or a series of point-to-point connections between the devices (e.g., RS-232, RS-485). In other cases, the hardwired connection 202 between the devices may be by way of optical fibers. In yet still other cases, the communicative connections between the touchless-interface controller 120 and the various other devices and controllers may take place wirelessly within the device cart, as shown by wireless connection 206. The wireless connection 206 may take any suitable form, such as wireless network operated under any suitable network specification (e.g., again, Bluetooth, IEEE 802.11). In some cases the touchless-interface controller 120, the resection controller 116, the video controller 118, and the pump controller 122 are designed and constructed to directly participate in the wireless connection 206. In other cases, external adapter modules may electrically couple to various devices to enable participation in wireless connections. Regardless of whether the example device cart 102 implements a hardwired connection 202, a wireless connection 204, or both, the communicative connections between and among the various devices are examples of a device-cart network.

The example resection controller 116 may control and provide operational power to both the mechanical resection instrument 104 and the ablation instrument 106. Each of the instruments may have a plurality of operational parameters selectable by the surgeon. For example, the mechanical resection instrument 104 may have operational parameters such as speed of the cutting element, rotational direction of the cutting element (e.g., clockwise or counter-clockwise), and an oscillate mode where the cutting element rotates back and forth about a particular rotational position. The ablation instrument 106 may have a plurality of operational parameters, such as the operational mode (e.g., ablate or coagulate), an aggressiveness or power setting within each mode, and alarm limits for ambient temperature within the joint as sensed by the ablation instrument 106 or calculated by the resection controller 116.

The video controller 118 is designed and constructed to interface with the arthroscope 108 (FIG. 1), such as by providing light which the arthroscope 108 directs into the surgical cavity, and receiving electronic images created by the camera head 110 (FIG. 1) based on light reflected from within the surgical cavity back through the arthroscope 108. The video controller 118, in turn, may display on the display device 114 the images captured by the camera head 110 to enable the surgeon to perform the surgical procedure. Nevertheless, the video controller 118 has a plurality of operational parameters, such as a zoom level of the images (e.g., a digitally-implemented zoom in and zoom out), a brightness of the displayed image (e.g., to reduce washout, or better illuminate the tissue within the displayed images), a snapshot feature to take a snapshot of a particular displayed image (e.g., a before image, and later an after image), and a video recording feature to record video of particular portions of the surgical procedure. Further still, the video controller 118 may implement video image enhancement, and thus the surgeon may need to turn on, turn off, and/or adjust the video image enhancement.

The pump controller 122 may be designed and constructed to provide fluid (e.g., saline) to the surgical site, pump fluid away from the surgical site, or both. In some cases, providing fluid may be through a dedicated cannula, and pumping fluid away from the surgical site may be through a separate dedicated cannula. In other cases, a single cannula device may be both a conduit for delivering fluid into the surgical site and pumping fluid away from the site. The pump controller 122 may be fluidly coupled to instruments used within the surgical site (e.g., the mechanical resection instrument 104 or the ablation instrument 106), and thus pumping fluid out of the surgical site may be though instruments. Regardless of the precise nature of the fluid connections to the surgical site, the pump controller 122 may have a plurality of operational parameters, such as fluid flow rate through the surgical site (e.g., to address visibility issues), a selectable lavage or rinse mode, pressure setpoint for pressure within the surgical site (e.g., to counter balance blood pressure to reduce bleeding into the surgical site, or to reduce the chances of extravasation).

In many cases the devices of the device cart 102 are outside the sterile field of the surgical procedure. Those persons that have "scrubbed in" to the sterile field, such as the surgeon, do not touch the devices outside the sterile field to reduce the chances of contamination. Thus, in the related art a circulating nurse may be assigned the task of making changes to any or all the operational parameters, at the direction of the surgeon. Other related-art systems have attempted to implement a hands-free system for changing parameters. Those related-art hands-free systems have shortcomings. For example, some related-art systems may receive voice commands, but the voice commands are structured commands (i.e., defined precisely in advance) and are used to navigate a menu structure to find and modify any particular operational parameters. Inasmuch as device carts may have several controllers therein, the menu structures may be several layers deep, and thus one needs to traverse several layers of menu structure to reach an operational parameter of interest. Other related-art hands-free systems project video of a menu structure into the sterile field, and the surgeon then navigates the layers of the menu structure by hand placement within the volumes associated with the each menu element. By contrast, various examples here are directed to touchless commands directed to a touchless-interface controller 120, where each touchless command directly identifies an operational parameter of a target surgical controller.

Figure 3:
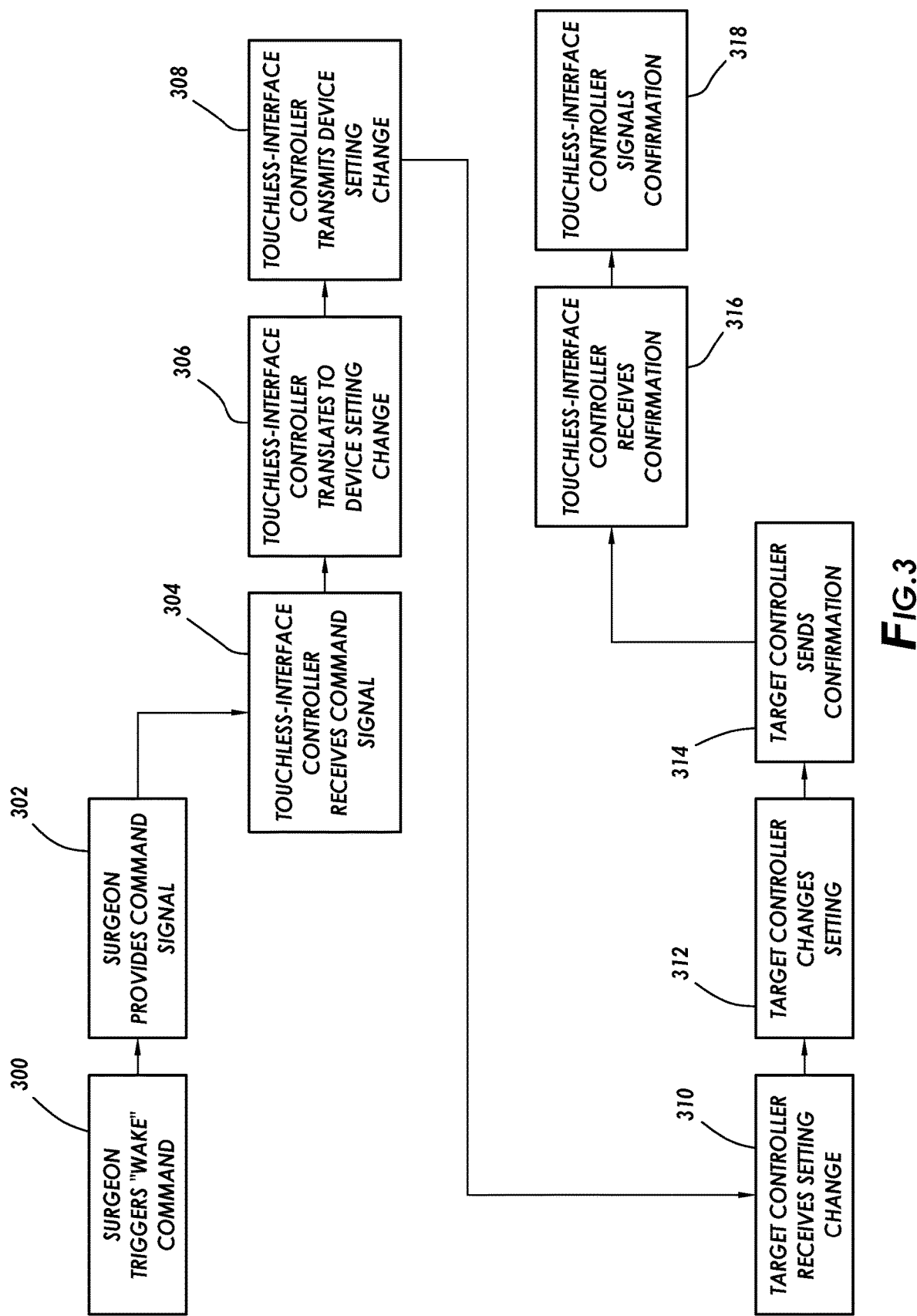
FIG. 3 shows, in block diagram form, a touchless-interface workflow in accordance with at least some embodiments.

FIG. 3 shows, in block diagram form, a touchless-interface workflow in accordance with at least some embodiments. In particular, the workflow starts (block 300) with the surgeon implementing a wake command. The wake command may take any suitable form. In one example, the wake command may be a verbal command received by the touchless-interface controller 120 (FIG. 1) by way of the microphone 200 (FIG. 2). For example, the surgeon may verbally pronounce a series of keywords, such as "Hey Smith & Nephew" as the wake command. The example verbal wake command is conceptually different than a natural-language command in that the wake command does not target or identify a particular operational parameter. However, the wake command in verbal form may nevertheless be provided in a natural-language form. In some cases, and as discussed below, the wake command may be a part of the overall touchless command received as a natural-language command, such as "Smith and Nephew, raise the joint pressure."

In yet still other cases, the wake command may be non-verbal. In one example, the wake command may be implemented by a surgeon's gaze dwelling upon a target surgical controller or a depiction of the target surgical controller for a predetermined amount of time. More particularly, in the further example the touchless-interface controller 120 (FIG. 1) may track the surgeon's gaze direction, such as by using the camera 112 (FIG. 1), or a dedicated eye tracking camera, such as disposed on a VR or AR headset. Regardless of the precise implementation, by tracking the surgeon's gaze the touchless-interface controller 120 may use gaze direction and gaze dwell as the wake command.

The next block in the example workflow of FIG. 3 is the surgeon providing a touchless command (block 302), where the touchless command directly identifies an operational parameter of a target surgical controller. The specification contemplates several touchless commands (e.g., natural-language commands, and hand gestures), and several example methods and related systems are discussed in greater detail below. For now, however, the specification continues in reference to just touchless command. The touchless-interface controller 120 (FIG. 1) receives the touchless command (block 304), and the touchless-interface controller 120 translates the touchless command to a device setting change or command value (block 306). For example, if the touchless command translates to a directive to raise the setpoint internal joint pressure provided by the pump controller 122, the touchless-interface controller 120 generates a corresponding command value. Once the touchless command has been translated (again block 306), the touchless-interface controller 120 then transmits the device setting change to the target controller (block 308).

The example target controller receives the device setting change or command value (e.g., by way of the device cart network) (block 310), and then implements the change indicated by the setting change or command value (block 312). In some cases, the command structure is open loop in the sense that once the setting change or command value is received (block 310) and implemented (block 312), the workflow may end. However, in yet still further cases the target controller may send a confirmation (block 314) that the setting change or command value was implemented. The confirmation may be sent in any suitable form, such as by using the device cart network. The touchless-interface controller 120 (FIG. 1) received the confirmation (block 316), and may then signal confirmation of the change to the surgeon (block 318). The signal confirmation may take any suitable form, such as an audible confirmation generated by the touchless-interface controller 120, or by the touchless-interface controller 120 sending information to the video controller 118 (FIG. 1) to be displayed on the display device 114 (FIG. 1).

Figure 4:
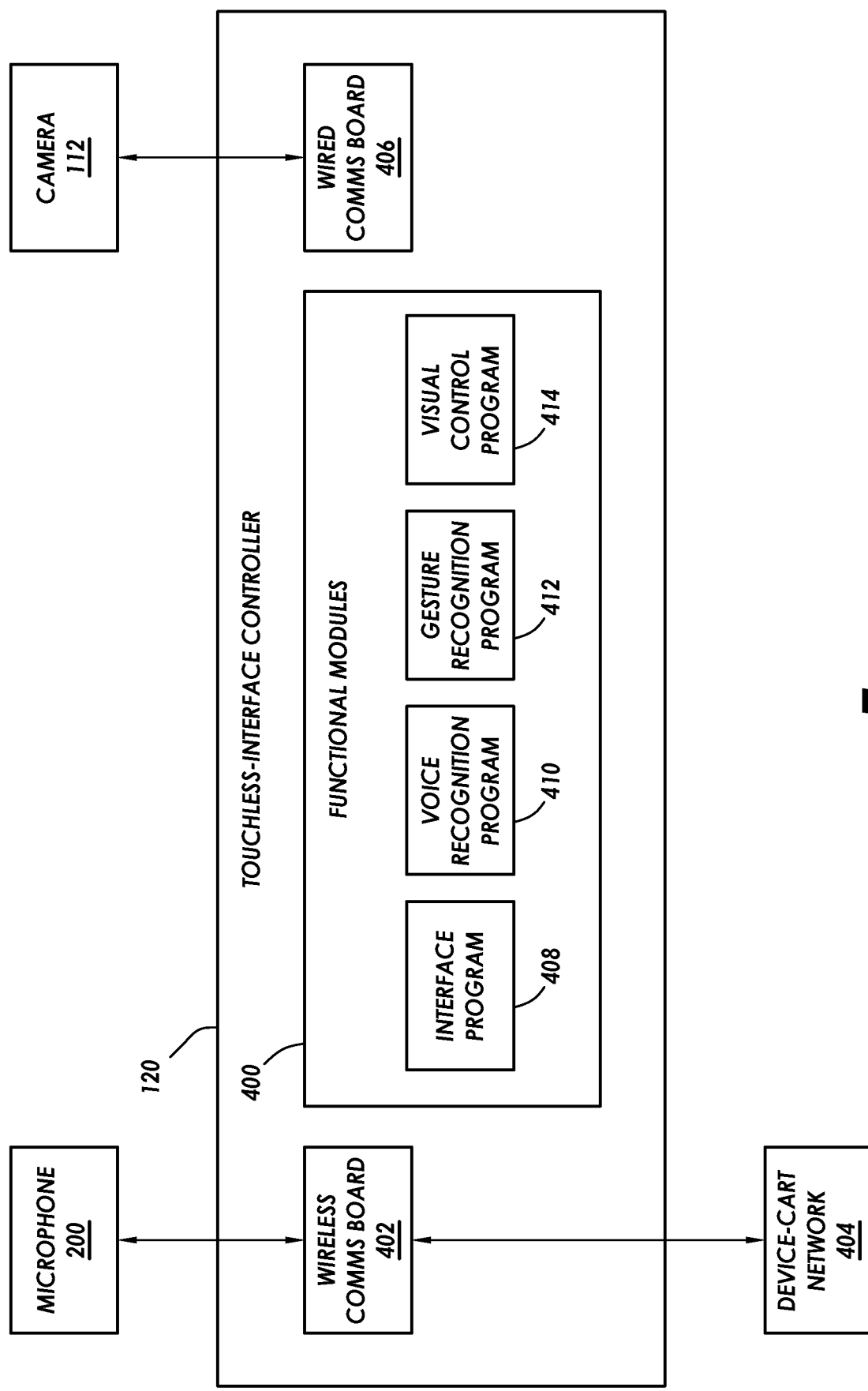
FIG. 4 shows a block diagram of example function modules of the touchless-interface controller in accordance with at least some embodiments.

FIG. 4 shows a block diagram of example function modules of the touchless-interface controller 120. In particular, the touchless-interface controller 120 may implement several functional modules 400 designed and constructed to enable the touchless-command structure. In some cases, the members of the functional modules 400 may be computer instructions executed on a general purpose processor (e.g., main processor, microcontroller, or reduced instruction set computer (RISC) processor) or a special purpose processor (e.g., a math processor, floating point unit, arithmetic unit). In other cases, the members of the functional modules 400 may be dedicated hardware (e.g., application-specific integrated circuit (ASIC), field-programmable gate array (FPGA)) designed and constructed to perform the specified tasks. In yet still other cases, the members of the functional modules 400 may be implemented as a combination of computer instructions and dedicated hardware systems. The functional modules 400 of the touchless-interface controller 120 communicate with external devices and systems by way of communication circuits or communication boards. For example, the touchless-interface controller 120 may implement a wireless communication board 402 ("wireless comms board" in the figure) designed and constructed to wirelessly communicate, such as wireless communication with the microphone 200, and wireless communication within the device cart network 404. Moreover, the touchless-interface controller 120 may implement a hardwired communication board 406 ("wired comms board" in the figure) designed and constructed to communicate hardwired connections, such as communication to the camera 112. The division between wireless communication and hardwired communication in FIG. 4 is merely an example, and as mentioned above the noted devices and controllers may communication with the touchless-interface controller 120 in any suitable wireless or hardwired form.

In the example system, the functional modules 400 may comprise an interface program 408, a voice recognition program 410, a gesture recognition program 412, and a visual control program 414. As the name implies, the interface program 408 is designed and constructed to interface between the various remaining modules of the functional modules 400 on the one hand, and the touchless-interface controller 120 and other devices and controllers of the device cart 102 (FIG. 1) on the other hand. More particularly, the example interface program 408 may receive touchless commands (e.g., from the microphone 200, the camera 112, or both), and send those touchless commands to the appropriate functional module. For example, received audio files may be provided to the voice recognition program 410. Received image files or video files may be provided to the gesture recognition program 412. Received visual information (e.g., gaze direction data) may be provided to the visual control program 414.

The example interface program 408 receives back from the various remaining modules translated commands in the form of command words or command values. Based on the command values the interface program 408 identifies a target controller, and communicates with the target controller over the appropriate communication board. In the example case of FIG. 4, once a target controller is identified, the interface program 408 communicates with the target controller using the wireless communication board 402 and device cart network 404.

The specification now turns to the voice recognition program 410, and more precisely to touchless commands provided to the voice recognition program 410 in the form of natural-language commands directly identifying an operational parameter of a target surgical controller. In the various examples, natural-language command means a spoken full or partial sentence that instructs a change of an operational parameter. In some cases, the natural-language commands include sentences where the subject is of the "you-understood" form. That is, the subject of the natural-language command is omitted from the utterance but understood from the context. For example, in the context of a surgical procedure using fluid pressure to distend a joint at the surgical site, "Turn up the joint pressure" is the "you-understood" form of "You turn up the joint pressure." In yet still further cases, given the context of a surgical procedure, natural-language commands may also include sentences where the verb is omitted but nevertheless understood from the context. For example, in the context of an endoscopic or arthroscopic surgical procedure, "recording on" includes both "you-understood" form and a "verb-understood" form to mean "You turn on the video recording" (the understood verb referred to as the verb-understood form).

In accordance with various examples, the voice recognition program 410 implements mapping of natural-language commands to command values. The following table provides a non-exhaustive list of example natural-language commands that may be received by the touchless-interface controller 120, an identity of a target controller, an identity of operational parameter of the target controller, and example command value associated with the natural-language command.

TABLE 1

| Touchless command | Target controller | Parameter | Command value |
| --- | --- | --- | --- |
| "Video on" | Video controller | Assert record-on | 001 |
| "Start recording" | Video controller | Assert record-on | 001 |
| "Take a picture" | Video controller | One-shot picture | 002 |
| "Take a snapshot" | Video controller | One-shot picture | 002 |
| "Shot" | Video controller | One-shot picture | 002 |
| "Zoom in" | Video controller | Zoom-level | 003 |
| "Oscillate" | Resection controller | Rotation direction | 004 |
| "Forward rotation" | Resection controller | Rotation direction | 005 |
| "Backward rotation" | Resection controller | Rotation direction | 006 |
| "Speed up the burr" | Resection controller | Burr-speed | 007 |
| "Burr speed increase" | Resection controller | Burr-speed | 007 |
| "Increase power" | Resection controller | Applied voltage | 008 |
| "More power" | Resection controller | Applied voltage | 008 |
| "Coagulate mode" | Resection controller | Ablation/coagulation mode | 009 |
| "Coagulate" | Resection controller | Ablation/coagulation mode | 010 |
| "Ablation mode" | Resection controller | Ablation/coagulation mode | 011 |
| "Ablate" | Resection controller | Ablation/coagulation mode | 012 |
| "Raise temperature alarm limit" | Resection controller | Joint temperature alarm setpoint | 013 |
| "Increase temperature alarm limit" | Resection controller | Joint temperature alarm setpoint | 013 |
| "Raise the pressure" | Pump controller | Joint pressure setpoint | 014 |
| "Increase joint pressure" | Pump controller | Joint pressure setpoint | 014 |
| "Increase flow" | Pump controller | Flow rate setpoint | 015 |
| "Lavage mode" | Pump controller | Flow rate setpoint | 016 |

Table 1 illustrates several aspects of the example cases. First, Table 1 illustrates that natural-language commands directed to the same operational parameter may take many forms—a many-to-one mapping or translation. For example, the natural-language commands "Video on" and "Start recording" have non-overlapping words, yet are directed to the operative parameter of the on- or active-state of video recording by the video controller 118 (FIG. 1). While only two example natural-language commands directed to the active-state of video recording by the video controller 118 are shown in Table 1, there may be two or more equivalent natural-language commands directed to the active-state of the video recording (e.g., "Record on", "Record this", "Begin saving video"). Similarly there, may be two or more equivalent natural-language commands directed to the off- or inactive-state of video recording by the video controller 118, but examples directed to the ceasing recording are not included so as not to unduly lengthen the table. Other examples of two or more equivalent natural-language commands include the example "Increase power" and "More power" natural-language commands directed to the resection controller 116 (FIG. 1), the "Coagulate mode" and "Coagulate" natural-language commands directed to the resection controller 116, and the "Raise the pressure" and "Increase joint pressure" natural-language commands directed to the pump controller 122 (FIG. 1). Again, however, there may be two or more equivalent natural-language commands, including some commands with non-overlapping words, directed to the same operational parameter.

The next implementation illustrated by Table 1 is that the example natural-language commands directly identify an operational parameter of a device or controller within the device cart 102 (FIG. 1), without requiring navigation through a multi-level menu structure. More particularly, the example natural-language commands directly identify an operational parameter of a target controller, and the natural language command does not contain reference to movement between levels of a menu structure. For example, the natural-language command "Lavage mode" directly addresses an operational parameter of the pump controller 122 (FIG. 1), the operational parameter being the flow-rate setpoint that implements a lavage mode. Lavage mode performs a high-flow rinse of the joint (e.g., quickly exchanges the fluid in the joint with fresh fluid), such as to remove blood and debris and thus increase the visibility within the joint. As yet another example, the natural-language command "Increase power" directly addresses an operational parameter of the resection controller 116 (FIG. 1) directed to the amount of power provided to the ablation instrument 106 (FIG. 1) (e.g., increasing the voltage setpoint of the active electrode(s) of the ablation instrument 106, or increasing the current setpoint of the ablation instrument 106).

The next implementation aspect shown by Table 1 is the mapping of the natural-language commands to command values. In particular, in accordance with example embodiments natural-language commands map to predetermined command values. To be clear, the natural-language commands are not predetermined words or predetermined utterances; rather, the natural-language commands directed to any particular operational parameter may take any suitable form, and the form may not be known in advance. Nevertheless, the family of natural-language commands that map to a change of a particular operational parameter in example cases result in a single command value. For example, the natural-language commands "Raise the pressure" and "Increase joint pressure" are both directed the pump controller 122 (FIG. 1) and particularly to increasing the joint pressure setpoint. In the example Table 1, increasing the joint pressure setpoint is arbitrarily assigned a command value 014. When the interface program 408 receives the example command value 014 from the voice recognition program 410, the interface program 408 knows to communicate with the pump controller 122 to request a predetermined increase (e.g., 5%) to the setpoint joint pressure. As another example, the natural-language command "Backward rotation" is directed to the resection controller 116 (FIG. 1) and particularly to the rotation direction parameter (likely a Boolean value). The example natural-language command maps to an arbitrary command value of 006. When the interface program 408 receives the example command value 006 from the voice recognition program 410, the interface program 408 knows to communicate with the resection controller 116 to request the rotational direction parameter be changed/adjusted to resent in reverse or backward rotation.

Referring again to FIG. 4, in accordance with various examples the voice recognition program may be a neural network or other artificial intelligence (AI) program designed to receive natural-language commands and generated therefrom command values. Thus, in some cases the neural network may be trained with a data set comprising several example natural-language commands for each change to an operational parameter, and the data set includes a predetermined command value assigned to the change to the operational parameter. By being trained with such a data set, the neural network may then receive natural-language commands, decode the device or controller to which the natural-language command is directed, decode the change to the operational parameter, and generate the predetermined command value.

In many cases, the devices and controllers of the device cart 102 (FIG. 2) operate as standalone devices that are not connected to the Internet. That is, for reasons of data privacy and security, in many cases computer systems within the surgical room are not connected to the Internet (at least when those devices are in the surgical room) and thus the computer systems are not accessible by other devices physically outside the surgical room. Thus, in some examples the touchless-interface controller 120 implementing the voice recognition program 410 performs its function related to processing of natural-language commands without sending or referring the natural-language command to a remote computer system (e.g., a cloud server or cloud processor). In legal jurisdictions where allowed, however, the task of processing the natural-language commands may be offloaded to remote computer systems.

The various example natural-language commands of Table 1 assume that the touchless-interface controller 120 has already been awakened by receiving the wake command (FIG. 3, block 300). However, in yet still further embodiments the natural-language command may further include the wake trigger words or phrase. For example, the natural-language command directed to raising the joint pressure setpoint, when including an example wake command, may take the form "Hey Smith & Nephew, raise the joint pressure." As another example, the natural-language command directed to changing to a coagulation mode for the ablation instrument 106 (FIG. 1), when including an example wake command, may take the form "Hey Smith & Nephew, change to coagulate mode." Thus, in such situations the natural-language commands need not be separated from the wake commands. In yet still other cases, the wake command may be provided by way a physical input, such as a foot switch or camera head button press.

Still considering the various example natural-language commands of Table 1, the natural-language commands directed to changes to non-Boolean parameters assume a predetermined amount of change. For example, the natural-language command "increase flow" may assume a predetermined increase in flow rate (e.g., 1% or 5%, or increase by a fixed amount such as an increase of 1 cubic centimeter (cc) per minute). However, in yet still further cases the natural-language command may include the amount of change requested by the surgeon. For example, regarding the zoom-level parameter a surgeon may provide the following example natural language command, "Zoom-in to 110%." In example embodiments, the voice recognition program 410 (FIG. 1) may thus return a two-part command value, comprising the command value directed to the video controller's zoom-level parameter (e.g., 003 from the Table 1) and an additional value representing new value for the parameter (e.g., 1.10 in the example). As another example, regarding the joint temperature alarm setpoint, a surgeon may provide the following example natural-language command, "Hey Smith and Nephew, increase the temperature alarm limit to 43° C." For this example, the voice recognition program 410 may thus return a two-part command value, comprising the command value directed to the resection controller joint temperature alarm setpoint (e.g., 013 from Table 1) and an additional value representing the new value for the parameter (e.g., 43 in the example). Many variations are possible, such as providing the additional value in the form of an amount of change rather than the directly identifying the full parameter.

The specification now turns to the gesture recognition program 412, and more precisely to touchless commands provided to the gesture recognition program 412 in the form of gestures directly identifying an operational parameter of a target surgical controller. In particular, in additional to or in place of the touchless commands in the form of natural-language commands, the various examples systems and methods may use gestures, such as hand gestures, to directly identify an operational parameter of a target surgical controller. Much like the natural-language commands, there is a significant amount of variation in which gestures to use and what each gesture means. The specification provides below several representative examples.

FIG. 5 shows an example had gesture in accordance with at least some embodiments. In particular, FIG. 5 shows an American sign language letter "P" and an associated motion. The example hand gesture starts on the left drawing with the letter "P" approximately horizontal to the ground, moves the middle drawing with the letter "P" pointing more downward, and then moves to the right drawing with the letter P again approximately horizontal. In an example case, the sign-language letter "P" rotated down and back up, perhaps several times, may refer to the pump controller, and specifically to lowering joint pressure setpoint.

FIG. 6 shows an example had gesture in accordance with at least some embodiments. In particular, FIG. 5 shows a sign language letter "P" and an associated motion. The example hand gesture starts on the left drawing with the letter "P" approximately horizontal to the ground, moves the middle drawing with the letter "P" pointing more upward, and then moves to the right drawing with the letter P again approximately horizontal. In an example case, the sign-language letter "P" rotated down and back up, perhaps several times, may refer to the pump controller, and specifically to raising the joint pressure setpoint.

FIGS. 5 and 6 show example hand gestures that directly identify an operational parameter of a device or controller within the device cart 102 (FIG. 1), without requiring navigation through a multi-level menu structure. More particularly, the example hand gestures directly identify an operational parameter of a target controller, and the natural language command does not contain reference to movement between levels of a menu structure. Much like the natural-language commands discussed with respect to Table 1, the example hand gestures map to command values. In accordance with example embodiments each hand gesture maps to predetermined command value. For example, decreasing the joint pressure setpoint (e.g., the hand gesture of FIG. 5) may be arbitrarily assigned a command value 014. When the interface program 408 (FIG. 4) receives the example command value 014 from the gesture recognition program 412 (FIG. 4), the interface program 408 knows to communicate with the pump controller 122 to request a predetermined increase (e.g., 5%) to the setpoint joint pressure.

Referring again to FIG. 4, in accordance with various examples the gesture recognition program 412 may be a neural network or other AI program designed to receive video containing hand gestures, and when a predefined hand gesture is present the gesture recognition program 412 generates command values based thereon. Thus, in some cases the neural network may be trained with a data set comprising video of the predefined hand gestures for each change to an operational parameter, and the data set includes a predetermined command value assigned to each predefined hand gesture. Inasmuch as the relationship of the camera 112 to the surgeon may be different as between surgical procedures, as well as within a particular surgical procedure, the data set may comprise several examples of each predefined hand gestures. By being trained with such a data set, during an actual surgical procedure the neural network may receive video containing hand gestures, decode the device or controller to which each hand gesture is directed, decode the change to the operational parameter, and generate the predetermined command value.

Again, in many cases the devices and controllers of the device cart 102 (FIG. 2) operate as standalone devices that are not connected to the Internet. Thus, in some examples the touchless-interface controller 120 implementing the gesture recognition program 412 performs its function related to processing of hand gestures without sending or referring the video of the hand gestures to a remote computer system (e.g., a cloud server or cloud processor). In legal jurisdictions where allowed, however, the task of processing the video of the hand gestures to recognize the predefined hand gestures may be offloaded to remote computer systems.

Still considering the example gestures and touchless commands, the hand gestures directed to changes to non-Boolean parameters assume a predetermined amount of change. For example, the example hand gestures to increase setpoint joint pressure as shown in FIG. 6 may assume a predetermined increase setpoint joint pressure (e.g., 1%, or 5%, or increase by a fixed amount). However, in yet still further cases the gestures may further include the amount change requested by the surgeon. For example, FIG. 7 shows a combination of the hand gestures for decreasing the setpoint joint pressure (in shorthand form) combined with a hand gesture representing a number (e.g., the number 3). In example embodiments, the gesture recognition program 412 (FIG. 4) may thus return a two-part command value, comprising the command value directed to the setpoint joint pressure and an additional value representing the change in value (e.g., change down by 3%). Many variations are possible, such as using sign language to provide a specific setpoint value.

Returning to FIG. 4, the specification now turns to the visual control program 414. In particular, the visual control program 414 may be used in several example ways. For example, and as mentioned above, the wake command provided to the touchless-interface controller 120 may be by way of the surgeon's gaze dwelling upon a particular device or controller within the device cart 102 (FIG. 1), or the surgeon's gaze dwelling upon a predetermined location (e.g., on the display device 114 (FIG. 1). In such cases, the interface program 408 may provide to the visual control program 414 a stream of video from which the surgeons gaze location may be determined. For example, the interface program 408 may receive a video stream from the camera 112 through the hardwired communication board 406, and provide the video stream to the visual control program 414. The visual control program 414 may, in turn, recognize a wake command based the surgeon's gaze dwelling upon a predetermined object (real or virtual) within the surgical room. Once the wake command is received, the visual control program 414 may alert the interface program 408 to begin forwarding video to the gesture recognition program 412, to begin forwarding representations of the sounds received by the microphone 200 to the voice recognition program, or both. The visual control program 414 may also implement additional functionality that is beyond or unrelated to the scope of this specification.

Figure 8:
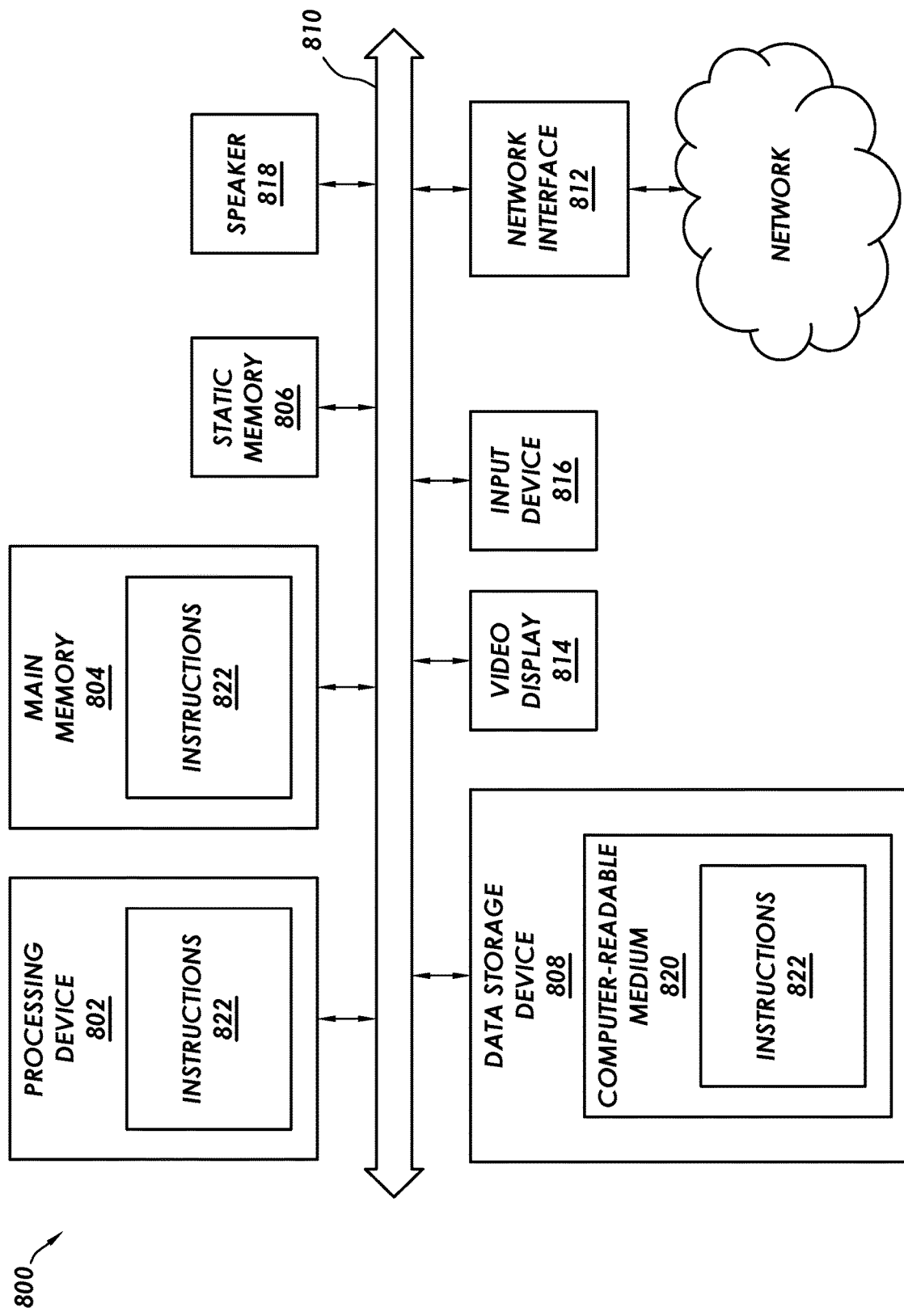
FIG. 8 shows an example computer system in accordance with at least some embodiments.

FIG. 8 shows an example computer system 800. In one example, computer system 800 may correspond to the touchless-interface controller 120 or the operative parts of the any of the devices and/controllers of the device cart 102. The computer system 800 may be connected (e.g., networked) to other computer systems in a local-area network (LAN), an intranet, and/or an extranet (e.g., device cart network 404), or at certain times the Internet (e.g., when not in use in a surgical procedure). The computer system 800 may be a server, a personal computer (PC), a tablet computer or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 800 includes a processing device 802, a main memory 804 (e.g., read-only memory (ROM), flash memory, dynamic random access memory (DRAM) such as synchronous DRAM (SDRAM)), a static memory 806 (e.g., flash memory, static random access memory (SRAM)), and a data storage device 808, which communicate with each other via a bus 810.

Processing device 802 represents one or more general-purpose processing devices such as a microprocessor, central processing unit, or the like. More particularly, the processing device 802 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 802 may also be one or more special-purpose processing devices such as an application specific integrated circuit (ASIC), a field programmable gate array (FPGA), a digital signal processor (DSP), network processor, or the like. The processing device 802 is configured to execute instructions for performing any of the operations and steps discussed herein. Once programmed with specific instructions, the processing device 802, and thus the entire computer system 800, becomes a special-purpose device, such as the touchless-interface controller 120 discussed.

The computer system 800 may further include a network interface device 812 for communicating with any suitable network (e.g., the device-cart network 404). The computer system 800 also may include a video display 814 (e.g., display device 114), one or more input devices 816 (e.g., a keyboard and/or a mouse), and one or more speakers 818. In one illustrative example, the video display 814 and the input device(s) 816 may be combined into a single component or device (e.g., an LCD touch screen).

The data storage device 808 may include a computer-readable storage medium 820 on which the instructions 822 (e.g., implementing any methods and any functions performed by any device and/or component depicted described herein) embodying any one or more of the methodologies or functions described herein is stored. The instructions 822 may also reside, completely or at least partially, within the main memory 804 and/or within the processing device 802 during execution thereof by the computer system 800. As such, the main memory 804 and the processing device 802 also constitute computer-readable media. In certain cases, the instructions 822 may further be transmitted or received over a network via the network interface device 812.

While the computer-readable storage medium 820 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

The above discussion is meant to be illustrative of the principles and various embodiments of the present invention. Numerous variations and modifications will become apparent to those skilled in the art once the above disclosure is fully appreciated. For example, while the touchless-interface controller 120 is shown and described as a separate controller within the device cart, in other cases the functionality of the touchless-interface controller may be incorporated into another controller within the device cart, such as the resection controller, the video controller, or any other device or controller associated with the surgical procedure. It is intended that the following claims be interpreted to embrace all such variations and modifications.

What is claimed is:

1. A method of performing a surgical procedure, the method comprising:
   receiving, by a touchless-interface controller, a touchless command directly identifying an operational parameter of a target surgical controller of a plurality of surgical controllers used for performing the surgical procedure, wherein the plurality of surgical controllers are (i) separate from the touchless-interface controller and (ii) configured to control respective devices in response to control commands received from the touchless-interface controller;
   generating, by the touchless-interface controller, a command value from the touchless command, wherein the command value is selected, based on the touchless command, from a plurality of predetermined command values;
   determining, by the touchless-interface controller and based on the command value, which of the plurality of surgical controllers is the target surgical controller; and generating and communicating, by the touchless-interface controller, a control command to the target surgical controller of the plurality of surgical controllers as determined by the touchless-interface controller based on the command value, wherein the control command as generated by the touchless-interface controller is a command to change the identified operational parameter of the target surgical controller.

2. The method of claim 1:
wherein receiving the touchless command further comprises receiving a natural-language command by way of a microphone communicatively coupled to the touchless-interface controller; and
wherein generating the command value further comprises generating the command value from a predefined list of command values using the natural-language command.

3. The method of claim 2 wherein the natural-language command does not contain reference to movement between levels of a menu structure.

4. The method of claim 2 wherein the generating the command value using the natural-language command further comprises generating the command value by the touchless-interface controller without the touchless-interface controller communicating the natural-language command to a remote computer system.

5. The method of claim 4:
wherein receiving the touchless command further comprises receiving a gesture by way of a camera communicatively coupled to the touchless-interface controller; and
wherein generating the command value further comprises generating the command value based on matching the gesture to a predefined list of gestures.

6. The method of claim 5 wherein receiving the gesture further comprises receiving a hand gesture that identifies both the target surgical controller and direction of change of a parameter associated with the target surgical controller.

7. The method of claim 1 further comprises, prior to receiving the touchless command, receiving a wake command by the touchless-interface controller.

8. The method of claim 7 wherein receiving the wake command further comprises receiving a verbal command by way of a microphone communicatively coupled to the touchless-interface controller.

9. The method of claim 7:
wherein receiving the touchless command further comprises receiving a natural-language command by way of a microphone communicatively coupled to the touchless-interface controller; and
wherein generating the command value further comprises generating the command value from a predefined list of command values using the natural-language command.

10. The method of claim 7:
wherein receiving the touchless command further comprises receiving a gesture by way of a camera communicatively coupled to the touchless-interface controller; and
wherein generating the command value further comprises generating the command value based on matching the gesture to a predefined list of gestures.

11. The method of claim 7 wherein receiving the wake command further comprises detecting, by the touchless-interface controller, that a surgeon's gaze has dwelled on the target surgical controller or a depiction of the target surgical controller for a predetermined amount of time.

12. The method of claim 7 wherein receiving the wake command further comprises receiving a physical input being at least one selected from a group comprising: a foot switch; and camera head button press.

13. A surgical system comprising:
a first surgical controller communicatively coupled to a device network;
a second surgical controller communicatively coupled to the device network;
a touchless-input device; and
a touchless-interface controller communicatively coupled to the device network and the touchless-input device, wherein the first and second surgical controllers are (i) separate from the touchless-interface controller and (ii) configured to control respective devices in response to control commands received from the touchless-interface controller the touchless-interface controller configured to:
receive a touchless command directly identifying an operational parameter of a target surgical controller of the first and second surgical controllers;
generate a command value from the touchless command, wherein the command value is selected, based on the touchless command, from a plurality of predetermined command values;
determine, based on the command value, which of the first and second surgical controllers is the target surgical controller; and
generate and communicate, by way of the device network, a control command to the target surgical controller as determined by the touchless-interface controller based on the command value, wherein the control command as generated by the touchless-interface controller is a command to change the identified operational parameter of the target surgical controller.

14. The surgical system of claim 13:
the touchless-input device further comprises a microphone;
wherein when the touchless-interface controller receives the touchless command, the touchless-interface controller is further configured to receive a natural-language command by way of the microphone; and
wherein when the touchless-interface controller generates the command value, the touchless-interface controller is further configured to generate the command value from a predefined list of command values using the natural-language command.

15. The surgical system of claim 14 wherein when the touchless-interface controller generates the command value using the natural-language command, the touchless-interface controller is further configured to generate the command value without the touchless-interface controller communicating the natural-language command to a remote computer system.

16. The surgical system of claim 14 wherein the natural-language command does not contain reference to movement between levels of a menu structure.

17. The surgical system of claim 13:
the touchless-input device further comprises a camera;
wherein when the touchless-interface controller receives the touchless command, the touchless-interface controller is further configured to receive a gesture by way of the camera; and
wherein when the touchless-interface controller generates the command value, the touchless-interface controller is further configured to generate the command value based on matching the gesture to a predefined list of gestures.

18. The surgical system of claim 17 wherein when the touchless-interface controller receives the gesture, the touchless-interface controller is further configured to receive a hand gesture that identifies both the target surgical controller and direction of change of a parameter associated with the target surgical controller.

19. The surgical system of claim 13 wherein the touchless-interface controller is further configured to receive a wake command.

20. The surgical system of claim 19 wherein when the touchless-interface controller receives the wake command, the touchless-interface controller is further configured to receive a verbal command by way of a microphone.

21. The surgical system of claim 19 wherein when the touchless-interface controller receives the wake command, the touchless-interface controller is further configured to detect that a surgeon's gaze has dwelled on the target surgical controller or a depiction of the target surgical controller for a predetermined amount of time.

22. The surgical system of claim 13 wherein the first and second surgical controllers are each at least one selected from a group consisting of: an arthroscopic video controller; an endoscopic video controller; a resection controller; an ablation controller; a Virtual Reality (VR) headset; an Augmented Reality (AR) headset; a Mixed Reality (MR) headset; a vacuum pump; a patient-positioning system; a robotic arm; an ultrasonic cutting device; an insufflator; a patient-positioning system; and a robotic surgical system.

* * * * *